(12) United States Patent
Priske et al.

(10) Patent No.: US 8,748,643 B2
(45) Date of Patent: Jun. 10, 2014

(54) METHOD FOR SEPARATION AND PARTIAL RETURN OF RHODIUM AND CATALYTICALLY EFFECTIVE COMPLEX COMPOUNDS THEREOF FROM PROCESS STREAMS

(75) Inventors: Markus Priske, Marl (DE); Götz Baumgarten, Haltern am See (DE); Alfred Kaizik, Marl (DE); Hans-Gerd Lüken, Marl (DE)

(73) Assignee: Evonik Oxeno GmbH, Marl (DE)

( * ) Notice: Subject to any disclaimer, the term of this patent is extended or adjusted under 35 U.S.C. 154(b) by 311 days.

(21) Appl. No.: 13/203,295

(22) PCT Filed: Feb. 25, 2010

(86) PCT No.: PCT/EP2010/052390
§ 371 (c)(1),
(2), (4) Date: Oct. 20, 2011

(87) PCT Pub. No.: WO2010/097428
PCT Pub. Date: Sep. 2, 2010

(65) Prior Publication Data
US 2012/0035382 A1    Feb. 9, 2012

(30) Foreign Application Priority Data

Feb. 27, 2009   (DE) .......................... 10 2009 001 230

(51) Int. Cl.
*C07F 15/00*      (2006.01)
*B01D 17/00*      (2006.01)

(52) U.S. Cl.
USPC ........................................ 556/13; 210/850

(58) Field of Classification Search
USPC ............................................ 556/13; 210/805
See application file for complete search history.

(56) References Cited

U.S. PATENT DOCUMENTS

| | | |
|---|---|---|
| 3,978,148 A | 8/1976 | Citron |
| 4,978,726 A | 12/1990 | Döhler et al. |
| 5,145,915 A | 9/1992 | Weitemeyer et al. |
| 5,146,005 A | 9/1992 | Weitemeyer et al. |

(Continued)

FOREIGN PATENT DOCUMENTS

| | | |
|---|---|---|
| DE | 23 11 388 | 9/1974 |
| DE | 198 01 437 | 7/1999 |

(Continued)

OTHER PUBLICATIONS

International Search Report issued Jul. 21, 2010 in PCT/EP10/052390 filed Feb. 25, 2010.

(Continued)

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The invention relates to a method for separating and partially returning transition metals and/or catalytically effective complex compounds thereof from a reaction mixture by combining one at least one-stage membrane separation and an adsorption, wherein a current comprising a catalyst, comprising a transition metal, is divided over at least one one-stage membrane separation step in a transition metal enriched retentate stream that resupplies the reaction mixture and a transition metal depleted permeate stream and the transition metal depleted permeate stream is further supplied to an adsorption step. The invention further relates to a method for producing tridecanals.

20 Claims, 6 Drawing Sheets

(56) References Cited

U.S. PATENT DOCUMENTS

| | | | |
|---|---|---|---|
| 5,215,667 A | 6/1993 | Livingston, Jr. et al. | |
| 5,260,402 A | 11/1993 | Weitemeyer et al. | |
| 6,211,322 B1 | 4/2001 | Döhler et al. | |
| 6,268,404 B1 | 7/2001 | Döhler et al. | |
| 6,310,261 B1 * | 10/2001 | Geissler et al. | 568/454 |
| 6,455,740 B1 | 9/2002 | Broeders et al. | |
| 7,250,204 B2 | 7/2007 | Brand et al. | |
| 7,276,541 B2 | 10/2007 | Döhler et al. | |
| 7,598,334 B2 | 10/2009 | Ferenz et al. | |
| 7,605,284 B2 | 10/2009 | Brueckner et al. | |
| 7,635,581 B2 | 12/2009 | Ferenz et al. | |
| 7,727,599 B2 | 6/2010 | Doehler et al. | |
| 7,759,402 B2 | 7/2010 | Venzmer et al. | |
| 7,776,989 B2 | 8/2010 | Ferenz et al. | |
| 7,838,603 B2 | 11/2010 | Schwab et al. | |
| 7,838,614 B2 | 11/2010 | Thum et al. | |
| 7,855,265 B2 | 12/2010 | Thum et al. | |
| 7,893,128 B2 | 2/2011 | Busch et al. | |
| 8,021,632 B2 | 9/2011 | Baumgarten et al. | |
| 8,138,294 B2 | 3/2012 | Henning et al. | |
| 8,172,936 B2 | 5/2012 | Herrwerth et al. | |
| 8,198,473 B2 | 6/2012 | Ferenz et al. | |
| 8,211,972 B2 | 7/2012 | Meyer et al. | |
| 2003/0018210 A1 | 1/2003 | Gelling et al. | |
| 2003/0049188 A1 | 3/2003 | Wiebus et al. | |
| 2004/0168981 A1 | 9/2004 | Dudziak et al. | |
| 2005/0136269 A1 | 6/2005 | Doehler et al. | |
| 2006/0155090 A1 | 7/2006 | Ferenz | |
| 2007/0059539 A1 | 3/2007 | Doehler et al. | |
| 2007/0123599 A1 | 5/2007 | Eilbracht et al. | |
| 2007/0149723 A1 | 6/2007 | Schwab | |
| 2007/0197678 A1 | 8/2007 | Cavaleiro et al. | |
| 2007/0295243 A1 | 12/2007 | Dohler et al. | |
| 2007/0299231 A1 | 12/2007 | Doehler et al. | |
| 2008/0187702 A1 | 8/2008 | Ferenz et al. | |
| 2008/0251456 A1 | 10/2008 | Wiese et al. | |
| 2009/0032465 A1 | 2/2009 | Baumgarten et al. | |
| 2009/0136757 A1 | 5/2009 | Wursche et al. | |
| 2010/0036011 A1 | 2/2010 | De Gans et al. | |
| 2010/0187174 A1 | 7/2010 | Wursche et al. | |
| 2010/0210445 A1 | 8/2010 | Von Rymon Lipinski et al. | |
| 2010/0248325 A1 | 9/2010 | Eckstein et al. | |
| 2010/0266651 A1 | 10/2010 | Czech et al. | |
| 2010/0298485 A1 | 11/2010 | Frey et al. | |
| 2011/0042004 A1 | 2/2011 | Schubert et al. | |
| 2011/0046305 A1 | 2/2011 | Schubert et al. | |
| 2011/0070175 A1 | 3/2011 | Herrwerth et al. | |
| 2011/0091399 A1 | 4/2011 | Meyer et al. | |
| 2011/0230619 A1 | 9/2011 | Kuppert et al. | |
| 2011/0230633 A1 | 9/2011 | Ferenz et al. | |
| 2011/0251070 A1 | 10/2011 | Poffenberger et al. | |
| 2011/0268642 A1 | 11/2011 | Brausch et al. | |
| 2012/0010302 A1 | 1/2012 | Hartung et al. | |
| 2012/0046503 A1 | 2/2012 | Priske et al. | |

FOREIGN PATENT DOCUMENTS

| | | |
|---|---|---|
| DE | 103 08 111 | 9/2004 |
| DE | 10 2005 046250 | 3/2007 |
| EP | 0 895 811 | 2/1999 |
| EP | 1 103 303 | 5/2001 |
| WO | 01 72679 | 10/2001 |

OTHER PUBLICATIONS

U.S. Appl. No. 13/386,523, filed Mar. 26, 2012, Grass, et al.
U.S. Appl. No. 13/498,690, filed Mar. 28, 2012, Kaizik, et al.
U.S. Appl. No. 13/513,225, filed Jun. 1, 2012, Haensel, et al.

* cited by examiner

METHOD FOR SEPARATION AND PARTIAL RETURN OF RHODIUM AND CATALYTICALLY EFFECTIVE COMPLEX COMPOUNDS THEREOF FROM PROCESS STREAMS

This application is a National Stage of PCT/EP10/052,390 filed Feb. 25, 2010 and claims the benefit of DE 10 2009 001 230.3 filed Feb. 27, 2009.

The present invention relates to the separation or concentration of transition metals or catalytically active complexes thereof from process streams by means of a combination of a membrane separation step and an adsorption step.

Particularly in rhodium-catalyzed hydroformylation, the recovery of the valuable rhodium from the product streams and discharge streams is an important process step which leads to an improvement in the value added.

Many documents are concerned with rhodium recovery. The processes are based on extraction (EP0147824, WO01056932), ion exchange (DE 195 43 15, U.S. Pat. No. 5,208,194, WO 02/096848, WO 02/020451), adsorption (U.S. Pat. No. 3,539,634) or filtration (FR 1588014).

The form in which the rhodium is present influences its adsorbability on the adsorbent. The temperature and the concentration of synthesis gas influence this (M. Beller, "Catalytic Carbonylation Reactions" in: Topics in Organometallic Chemistry, 18, (2006)).

DE 95 36 05 describes the precipitation of dissolved rhodium by depressurization and heating of the product stream and also the adsorption by means of silica gel or activated carbon. Achievable degrees of precipitation and loading capacities are not mentioned. Heating can lead to undesirable aldol condensation of the product.

In GB 801 734 and FR 1 588 014, precipitation of the rhodium as metal is achieved by heating with water. The rhodium precipitates are subsequently removed from the product by means of decanters, filtration or centrifuges. The introduction of water leads not only to the necessity for a further thermal product work-up step but also to the catalyst no longer being able to be recirculated to the reaction since even traces of water can destroy the active catalyst species.

If the adsorption of rhodium is carried out under a hydrogen atmosphere, the adsorbed rhodium can, according to DE 22 62 852, be converted into soluble rhodium carbonyl complexes. As adsorbents, mention is made by way of example of activated carbon, silica gel, aluminum oxide, kieselguhr and magnesium oxide. In the examples, the influence of the hydrogen atmosphere during the adsorption is not demonstrated. In addition, the reaction in the examples is in an aqueous system which cannot be applied, for example, to ligand-modified hydroformylation reactions.

DE 23 11 388 describes the selective adsorption of rhodium-tert-phosphine catalysts on oxides and carbonates of the elements of main groups II and III of the Periodic Table and also silicates and alkaline earth metals. The process is very complicated since the catalyst has to be rinsed from the absorbent by means of special solvents and subsequently has to be separated from this solvent. These additional steps can damage the catalyst. In addition, the loading capacities of the adsorbent are very low, which all leads to an uneconomical process.

U.S. Pat. No. 4,388,279 describes the extraction of rhodium by means of a concentrated aqueous ammonia solution with subsequent adsorption on calcium sulfate. The process is very complicated and the degrees of separation are very low at from 71 to 75%. In addition, nothing is said about the loading capacity of the adsorbent.

The use of activated carbon for the adsorptive separation of rhodium from a process for preparing 1,4-hexadiene from ethylene and 1,3-butadiene at temperatures of from $-20°$ C. to $+120°$ C. is disclosed in U.S. Pat. No. 3,978,148. The degrees of separation achieved here are rather unsatisfactory. In the best example, the rhodium concentration in the discharged solution is still 27 ppm. In addition, in the case of the activated carbon beds used, immediate breakthrough of the rhodium with an extremely rapid increase in the rhodium concentration in the eluate takes place, which can in turn be attributed to a very low loading capacity of the activated carbon. There is no possibility of direct recycling to the reaction.

WO 01/72679 describes a process for recovering rhodium from hydroformylation products. The process is characterized in that the hydroformylation products are heated at temperatures of from 50 to 200° C. in the presence of a solid adsorbent. The loading capacity of the activated carbon used is not mentioned as a critical factor for the economics of the process. The process likewise has the disadvantage that direct recirculation of the rhodium which has been separated off to the reaction is not possible.

EP 1 669 337 describes a process for the adsorption of cobalt. The degree of deposition of cobalt on activated carbon is very low at less than 9%.

Further documents describe the recovery of rhodium by precipitation on tellurium or sulfur (DE 32 23 501, DE 29 11 193). These processes are complicated and costly and difficult to implement in practice. The precipitated rhodium also has to be worked up in a complicated manner before it can be introduced as active catalyst into the reaction.

The disadvantage of a process based solely on an adsorption step, in particular for the recovery of rhodium, is the complete loss of the catalytic activity of the adsorbed metal. A complicated and costly metallurgical work-up is necessary for renewed use as hydroformylation catalyst. In addition, there is an increased tie-up of capital.

The disadvantage of a membrane separation based solely on nanofiltration is the fact that the separation can in principle not be complete. If this disadvantage is countered by use of multistage processes, the capital and operating costs increase greatly with the number of stages and therefore the amount of rhodium retained.

The technical object of the invention is to provide a process for concentrating transition metal-based homogeneous catalysts, in which the catalyst system can be concentrated or separated off with retention of its activity. The process of the invention displays a high degree of retention for the catalyst system and ideally avoids decomposition thereof.

This technical object is achieved by a process for separating off and partly recirculating transition metals and/or catalytically active complexes thereof from a reaction mixture by a combination of an at least single-stage membrane separation and an adsorption, wherein a catalyst-containing stream containing a transition metal is separated by means of at least one single-stage membrane separation step, in particular a nanofiltration, into a retentate stream enriched in transition metal, which is returned to the reaction mixture, and a permeate stream depleted in transition metal and the permeate stream depleted in transition metal is fed to an adsorption step.

The combination according to the invention of a membrane separation step by means of nanofiltration with an adsorption step is advantageous. The nanofiltration keeps a major part of the rhodium in the product and discharge streams in the process. Adsorption on ashable adsorbents is particularly suitable for recovering the remaining rhodium from the permeate stream from the nanofiltration.

Transition metals, in particular rhodium, in the permeate stream from a nanofiltration can:
(i) be bound to ligands,
(ii) be partly bound to ligands, or
(iii) be present in free form in the organic phase.

As a result of the process, the permeate stream from a nanofiltration is characterized in that it is free of solids. Only dissolved transition metal, in particular rhodium, and no particulate transition metal is therefore present in the permeate stream.

As a person skilled in the art will know, the ratio of adsorption to desorption improves at relatively low temperatures. This effect can be advantageously exploited in the process of the invention by heating in an intermediate step between nanofiltration and adsorption since the adsorption of transition metals, in particular rhodium, occurs after the thermal treatment.

In a particular embodiment of the process for separating off and partly recirculating transition metals or catalytically active complexes thereof, the metal component is retained to an extent of at least 60% by mass in the retentate stream from a reaction mixture comprising high boilers and a catalyst system by means of a membrane separation step which contains one or more membranes and is made up of one or more stages. The permeate stream from this membrane separation step is worked up in the subsequent adsorption step where at least 60% by mass of the metal component fed in is retained by the adsorbent. For the purposes of the invention, high boilers are materials which have boiling points higher than those of the primary hydroformylation products (aldehydes and/or alcohols having one more carbon atom than the olefin used) and have higher molar masses and are formed during the hydroformylation. These include aldolization products and acetalization products, ethers and also esters formed by reaction of alcohols and acids, with the alcohols and acids being formed by disproportionation of aldehydes. High boilers present in process streams from hydroformylation generally have boiling points above 55° C. at 0.1 MPa.

The separation in the membrane separation step is carried out with a separation limit of from 200 to 2000 g/mol in the temperature range from 40 to 150° C. and in a transmembrane pressure range from 0.5 to 7.0 MPa. The permeate stream from the membrane separation step is fed to an adsorption step and the adsorption is carried out at a temperature of from 30 to 140° C. and space velocities of from 0.01 to 5 l/h. The adsorbent is preferably used as a fixed bed.

As adsorbent, it is possible to use, in particular, activated carbon, high-surface-area polysilicic acids such as silica gels (silica xerogels), finely divided silica, high-surface-area aluminum oxides and aluminum oxide hydrates and also used or fresh (hydrogenation) catalysts.

Particularly advantageous adsorbents have been found to be chemically modified silica materials as are disclosed in WO 2006013060 A1. Such adsorbents can be obtained under the product name mercaptoalkyl-modified silica, type Rh H3, batch no. 09-S26-001 from PhosphonicS Ltd, 114 Milton Park, Abingdon, OXON, OX14 4SA, United Kingdom.

The membrane separation step can be carried out using a membrane, two or more membranes or using one, two or more membrane separation step(s). In the process of the invention, it is possible, in particular, for two or more membrane separation steps to be carried out. The membrane separation steps can be carried out in direct succession. The arrangement in series can be carried out by either the retentate stream or the permeate stream, preferably the permeate stream, from the first membrane separation step being fed as feed stream to a further membrane separation step. Any membrane separation steps following the first membrane separation step according to the invention can likewise be carried out under similar conditions to the first. One membrane or a plurality of membranes can be used in a membrane separation step. Preference is given to using two or more membranes in a membrane separation step.

In the case of a multistage membrane separation step, it can be advantageous to use membranes having different separation limits and/or permeabilities in the membrane separation steps.

In the process of the invention, it is possible to use membranes which, owing to their chemical and/or physical properties, are suitable for retaining metal complex catalysts and/or free organophosphorus ligand, preferably to an extent of at least 60% by mass. A further prerequisite for usability of the membrane is that the membrane has to be stable toward all compounds present in the hydroformylation reaction mixture, in particular to the solvents.

Preference is given to using membranes which have a separation-active layer of a material selected from among cellulose acetate, cellulose triacetate, cellulose nitrate, regenerated cellulose, polyimides, polyamides, polyether ether ketones, aromatic polyamides, polyamideimides, polybenzimidazoles, polybenzimidazolones, polyacrylonitrile, polyaryl ether sulfones, polyesters, polycarbonates, polytetrafluoroethylene, polyvinylidene fluoride, polypropylene, polydimethylsiloxane (PDMS), polyether ether ketone (PEEK), acrylonitrile-glycidyl methacrylate (PANGMA), silane-hydrophobized ceramic membranes as are described in DE 103 08 111, polymers having intrinsic microporosity (PIM) and others as are described, for example, in EP 0 781 166 and in "Membranes" by I. Cabasso, Encyclopedia of Polymer Science and Technology, John Wiley and Sons, New York, 1987.

Particular preference is given to using membranes which have, as separation-active layer, a polymer layer of polydimethylsiloxane (PDMS), polyimide (PI), polyamideimide (PAI), acrylonitrile-glycidyl methacrylate (PANGMA), polyamide (PA) or polyether ether ketone (PEEK) and are made up of polymers having intrinsic microporosity (PIM) or in which the separation-active layer is made up of a hydrophobized ceramic membrane. Very particular preference is given to using membranes comprising silicones or polyamideimide. Such membranes are commercially available. Apart from the abovementioned materials, the membranes can comprise further materials. In particular, the membranes can have support materials to which the separation-active layer has been applied. In the case of such composite membranes, a support material is present in addition to the actual membrane. A selection of support materials is described in EP 0 781 166, which is explicitly incorporated by reference. Furthermore, reinforcing materials such as particles of inorganic oxides or inorganic fibers such as ceramic or glass fibers which increase the stability of the membrane, in particular to pressure fluctuations or high differential pressures, can be present in the membranes used according to the invention.

The adsorption step can be carried out in one or more batch vessels or preferably in one or more fixed beds. When using a plurality of batch vessels and/or fixed beds, a parallel or series arrangement is possible.

The separation power of the adsorption step can be increased by recirculation of the eluate to upstream of the adsorption step.

It is advantageous to use activated carbon as adsorbent. Firstly, activated carbon is inexpensive and available in large quantities. Secondly, recovery of the adsorbed metal can be effected by ashing of the loaded activated carbon. Examples of activated carbons which are used and are commercially available are shown in table 1:

TABLE 1

| Supplier | Trade name | Molasses No. [mg] | Iodine No., min. [mg/g] | BET [m²/g] |
|---|---|---|---|---|
| Norit | GAC 1240 W | | 950 | 1100 |
| Norit | Gran | 150 | | 1400 |
| Chemviron | CPG ® LF | 210 | 950 | 950 |
| Chemviron | AquaCarb | | 1100 | 1100 |
| Chemviron | CAL ® I | 250 | 1050 | 1050 |
| Fluka | 18002 | | 1040 | |

The molasses number and the iodine number are generally accepted analytical parameters for describing the adsorption behavior of activated carbon. Further details may be found, for example, in EP 1 280 593 B1 or DE 34 18 150 A1.

As an alternative, a chemically modified silica material which can be obtained under the product name mercaptoalkyl-modified silica, type Rh H3, batch No. 09-S26-001 from PhosphonicS Ltd, 114 Milton Park, Abingdon, OXON, OX14 4SA, United Kingdom, can be used as adsorbent. This material is described in more detail in WO 2006013060 A1. The relevant disclosure content of this document is incorporated by reference.

Depending on the catalytically active complex, it can be advantageous to leave the stream depleted in transition metal from the membrane separation step to reside in an intermediate vessel in order to convert the transition metal or catalytically active complexes thereof into readily adsorbable species. The further addition of ligands may also have an advantageous effect on the adsorbability.

Figure 1:
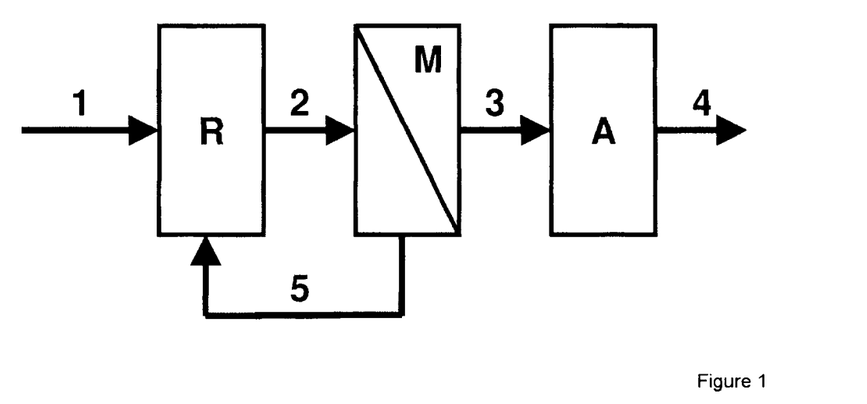

In FIG. 1, the starting materials for the hydroformylation, viz. olefins and synthesis gas, (1) are fed to the reactor (R). Hydroformylation of the olefins to form aldehydes takes place in the presence of the catalytically active complexes initially placed in the reactor. Aldehydes and also by-products and subsequent products, including high boilers such as aldol condensation products, unreacted starting materials and the catalytically active complexes are discharged (2) as reaction mixture from the reactor and fed to a membrane separation step (M). Here, concentration of the transition metal or catalytically active complexes takes place on the retentate side (5) and depletion of the transition metal or the catalytically active complexes takes place on the permeate side (3). The stream (3) depleted in transition metal or catalytically active complexes is fed to the adsorption step (A) from which the stream (4) which has been further depleted in transition metal or catalytically active complexes flows out.

Figure 2:
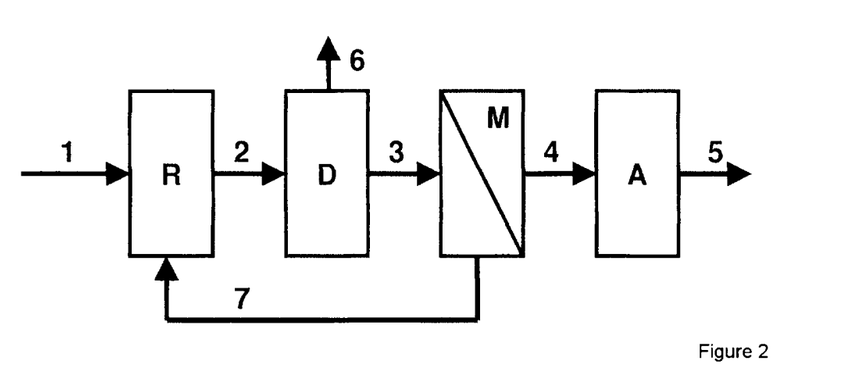

Should direct separation of the high boilers from the hydroformylation product aldehyde be necessary, FIG. 2 shows a preferred process arrangement. The starting materials for the hydroformylation, viz. olefins and synthesis gas, (1) are fed to the reactor (R). The hydroformylation of the olefins to form aldehydes takes place in the presence of the catalytically active complexes initially placed in the reactor. Aldehydes and by-products and subsequent products including high boilers such as aldol condensation products, unreacted starting material and the transition metal or catalytically active complexes thereof are discharged (2) as reaction mixture from the reactor and fed to a thermal separation step (D). In the thermal separation step, the reaction mixture (2) is separated into a stream (3) which is enriched in relatively high-boiling components such as the above-described by-products of the reaction and in transition metal and/or catalytically active complexes thereof and a product stream (6) containing lower-boiling components, predominantly aldehydes. The high boiler stream (3) is fed to a selective membrane separation step (M). Here, concentration of the transition metal or catalytically active complexes thereof takes place on the retentate side (7) and depletion of the transition metal or catalytically active complexes thereof takes place on the permeate side (4). The stream (4) depleted in transition metal or catalytically active complexes is fed to the adsorption step (A) from which the stream (5) which has been further depleted in transition metal or catalytically active complexes flows out.

The process of the invention for separating off and partly recirculating, in particular, rhodium and catalytically active complexes thereof from reaction mixtures from hydroformylation processes by means of a combination of a membrane separation step and an adsorption step will be illustrated by way of example below for the rhodium complex-catalyzed hydroformylation of $C_{12}$-containing olefin mixtures.

This subject matter of the invention is the use of the process of the invention in the preparation of mixtures containing tridecanals and tridecanols, as presented, for example, in EP 1 515 934 B1, wherein the removal of the rhodium-containing catalyst complex comprises the following steps:

a) thermal separation of the product mixture containing tridecanals and tridecanols from the reaction mixture from the hydroformylation;
b) at least single-stage membrane separation which is carried out over at least one membrane so that at least 60% by mass of the rhodium used remains in the retentate stream;
c) introduction of the permeate stream obtained into a subsequent adsorption step so that at least 60% by mass of the rhodium present in the permeate stream is retained;
d) recirculation of the retentate stream with the concentrated rhodium-containing catalyst complex from step b) to the hydroformylation reaction.

It is advantageous for the membrane separation step of the process of the invention to be carried out at a transmembrane differential pressure of more than 1.5 MPa. A high transmembrane differential pressure leads, firstly, to increased retention of the transmission metal or catalytically active complexes thereof and, secondly, to an increased permeate flow per unit area of membrane used.

Even without further details, it is assumed that a person skilled in the art can utilize the above description in its widest scope. The preferred embodiments and examples are therefore to be interpreted merely as descriptive disclosure which does not constitute any limitation. The present invention is illustrated below with the aid of examples. Alternative embodiments of the present invention can be obtained in an analogous way.

EXAMPLES

Example No. 1 According to the Invention

Figure 3:
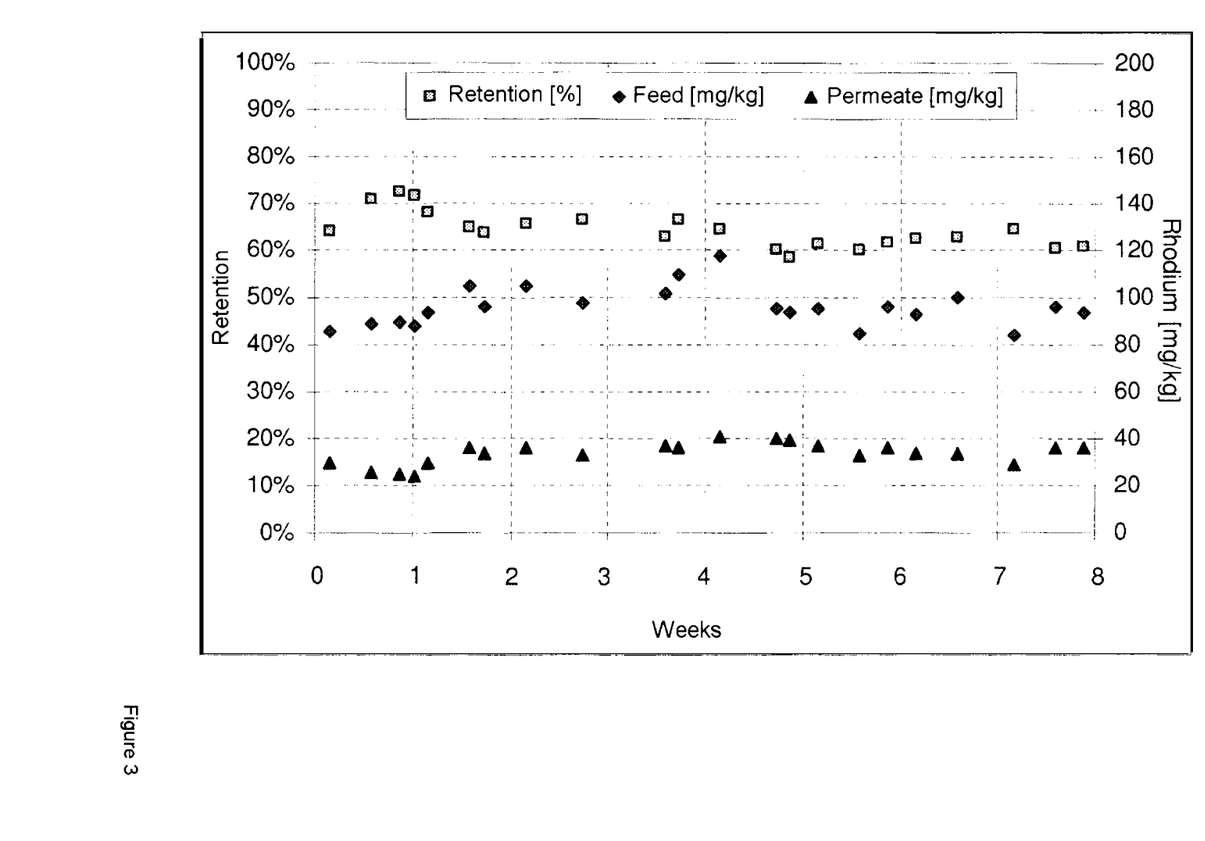

The separation task as per FIG. 2 was selected as example. The reaction is a rhodium-phosphite-catalyzed hydroformylation of a $C_{12}$-containing olefin mixture as described, for example, in EP 1 515 934 B1. The rhodium precursor used is acetylacetonatodicarbonylrhodium and the ligand used is tris (2,4-di-tert-butylphenyl)phosphite. The rhodium concentration was 10 mg/kg based on the reaction mixture. The ligand to rhodium ratio was 20:1. The aldehyde mixture of tridecanals and by-products and subsequent products including high boilers such as aldol condensation products, unreacted starting material and rhodium or the catalytically active complexes are fed to a thermal separation step. The bottoms enriched in high boilers and rhodium or the catalytically active complexes (about 100 ppm) is fed to the combined membrane separation and adsorption step. The proportion of high boilers is above 50% by mass. The molar mass difference between the active catalyst species and the high boilers is less than 500 g/mol. It was able to be shown by way of example that more than 60% by mass of the catalyst in the high boiler stream is retained by means of a single-stage membrane separation step using a radiation-chemically modified silicone composite membrane (supplied by GMT, type oNF2), as is described, for example, in DE 195 07 584 C2, at a temperature of 80° C., a transmembrane pressure of 2.0 MPa and a flow over the membrane of 1.7 m/s (FIG. 3).

Figure 4:
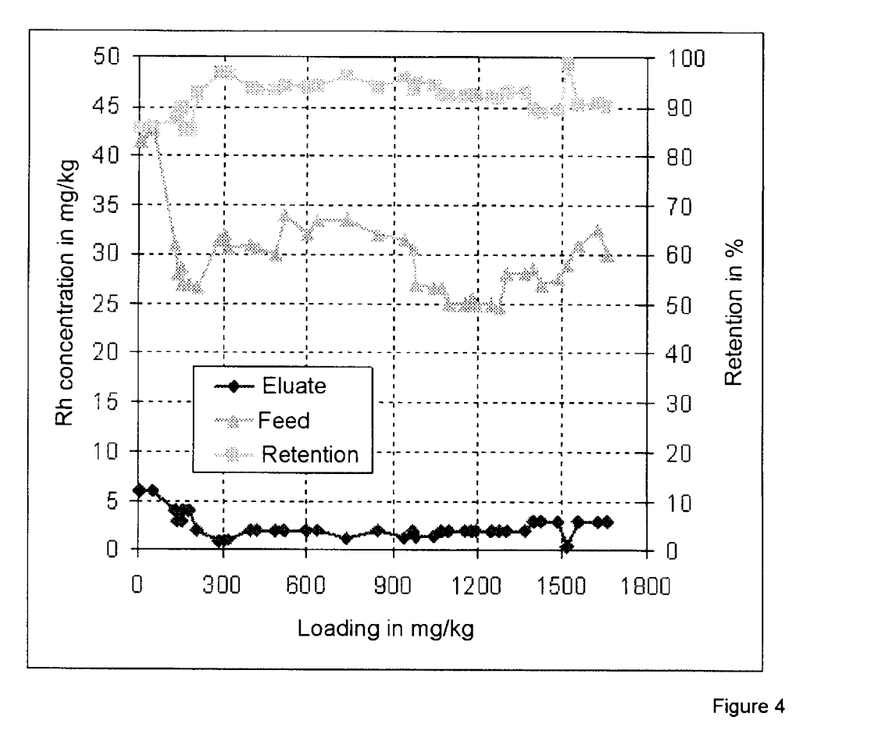

The catalyst-containing permeate stream was passed at a space velocity of about 0.1 $m^3/(m^3h)$ through a 1 m high activated carbon bed composed of 614 g of granulated activated carbon (supplied by Fluka, activated carbon granulated, purum, catalogue 18002, batch 52980), resulting in a further 85 to 99% by mass of the catalyst being retained. In the experiments, loadings of the activated carbon with rhodium of more than 1.5 mg/kg were achieved (see FIG. 4).

Figure 5:
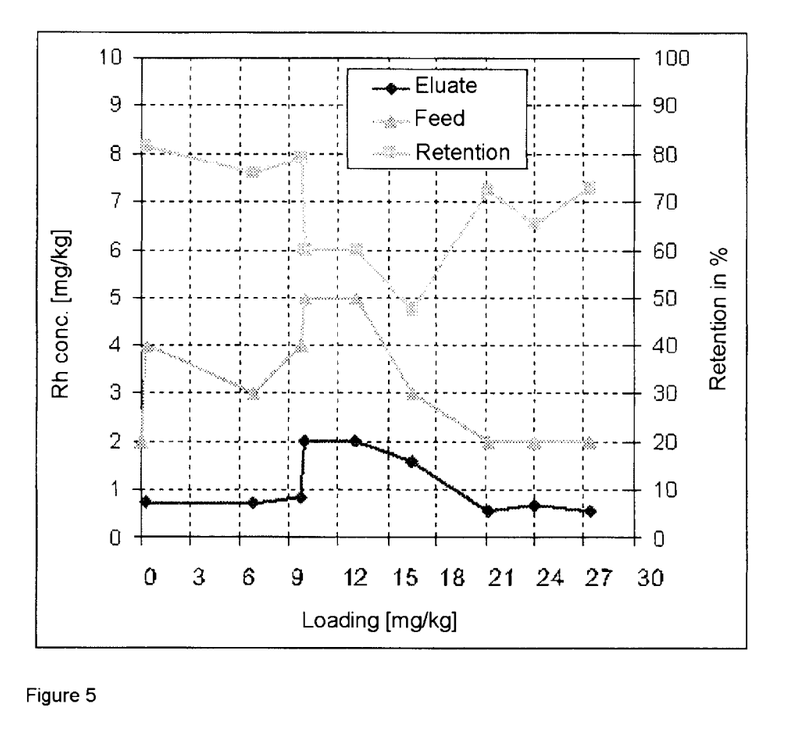

If the rhodium-depleted eluate obtained in this way is passed at a space velocity of about 0.1 $m^3/(m^3h)$ through a 1 m high activated carbon bed composed of a further 614 g of granulated activated carbon (same type), the rhodium content is reduced by a further 50-80% (see FIG. 5).

Example No. 2 According to the Invention

Figure 6:
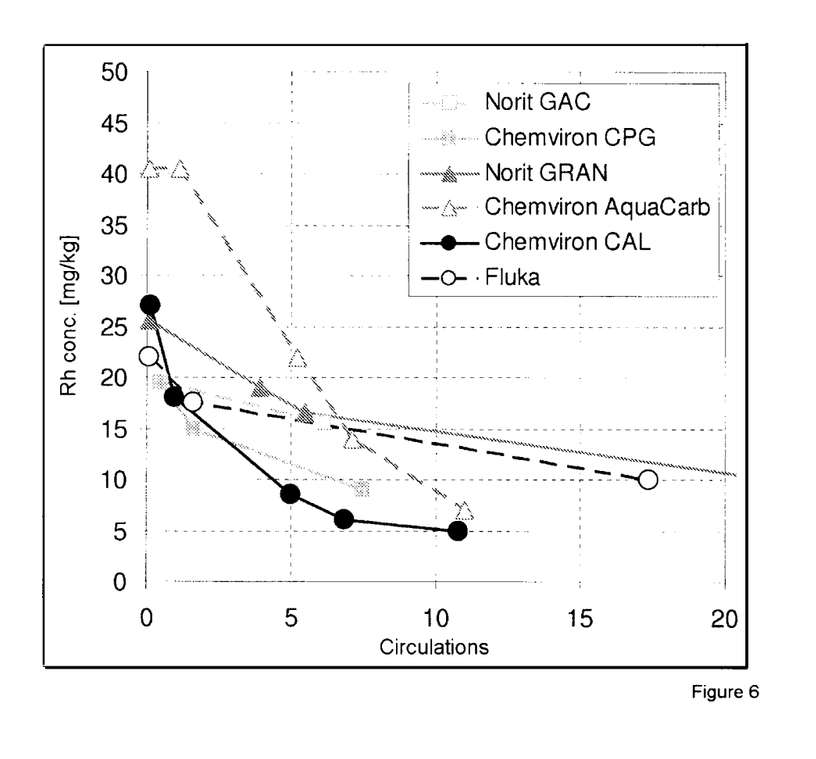
Figure 7:
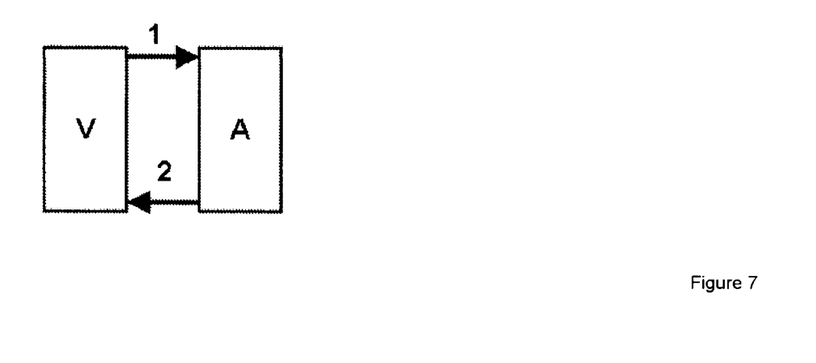

In this example, some further, commercially available activated carbon grades (see table 1) were supplied from a batch vessel (V) as per FIG. 7 with a permeate stream 1 obtained in a manner analogous to the preceding example. 60 g of activated carbon were used in each case at a space velocity of 1 $m^3/(m^3h)$. The eluate obtained, stream 2, was recirculated a number of times through the activated carbon bed A, resulting in the rhodium concentration in the eluate decreasing significantly with increasing number of circulations (FIG. 6).

For a given activated carbon bed, low rhodium concentrations in the eluate can preferably be achieved for a given feed stream by means of batchwise operation with recirculation of the eluate.

Example No. 3 According to the Invention

Figure 8:
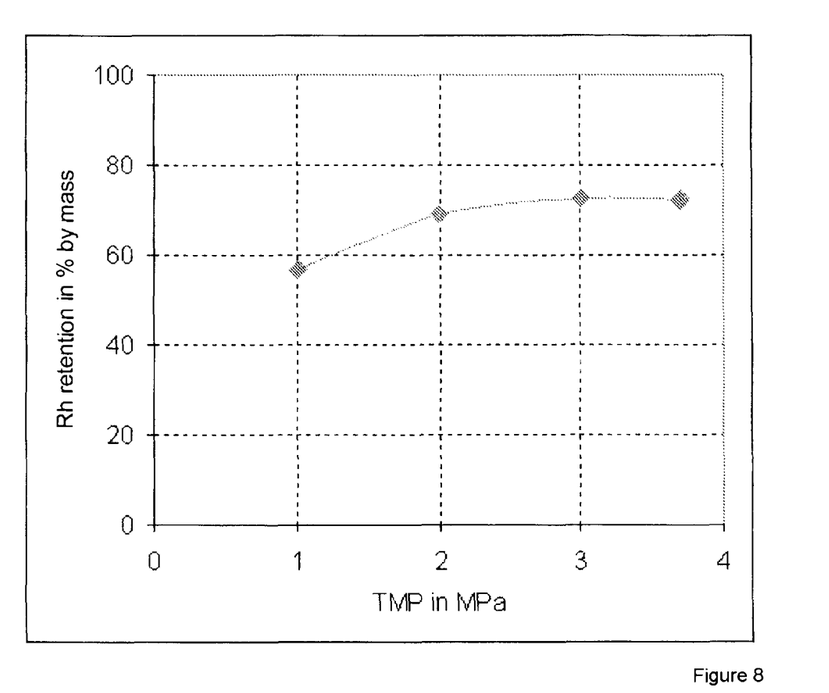

The bottom stream obtained in a manner analogous to example No. 1 was passed in a membrane separation step at various transmembrane pressures (1 MPa, 2 MPa, 3 MPa, 3.7 MPa) over a radiation-chemically modified silicone composite membrane (supplied by GMT, type oNF2). Here, significantly better rhodium retentions were obtained at higher transmembrane pressures, as shown in FIG. 8.

Example No. 4 According to the Invention

In a further example according to the invention, the permeate stream produced as described in example 1 was passed:
in case A directly and
in case B with prior heating at 90° C. for 24 hours in a single pass through a 60 g activated carbon bed at a space velocity of 1 $m^3/(m^3h)$ and a bed temperature of 100° C.

The permeate stream containing 40 mg/kg of rhodium was in case A depleted to 14 mg/kg and in case B depleted to 6 mg/kg.

Example No. 5 According to the Invention

A bottom product enriched in high boilers and rhodium complex catalyst obtained as described in example 1 was fed to a two-stage membrane filtration operated in a manner analogous to example 1. A rhodium retention of about 90% was achieved here. The now depleted permeate stream was fed at a temperature of 70° C. at a space velocity of 0.5 $m^3/(m^3h)$ to a bed of a chemically modified silica material (mercaptoalkyl-modified silica, type Rh H3, batch No. 09-S26-001 from PhosphonicS). The rhodium concentration in the eluate was less than 0.5 ppm. This corresponds to a total rhodium retention of more than 99%.

The invention claimed is:

1. A process for separating off and partly recirculating at least one selected from the group consisting of a transition metal and a catalytically active complex of a transition metal, from a reaction mixture, the process comprising:
   separating the reaction mixture, which comprises a catalyst-comprising stream that comprises the at least one transition metal and the catalytically active complex by applying the reaction mixture to at least a single-stage membrane,
   to yield (i) a retentate stream enriched in transition metal, and (ii) a permeate stream depleted in transition metal but that comprises some transitional metal;
   returning the retentate stream to the reaction mixture; and
   feeding the permeate stream to an absorbent material to absorb the transitional metal.

2. The process of claim 1, wherein the transition metal is rhodium.

3. The process of claim 1, wherein at least 60% by mass of the transitional metal remains in the retentate stream in the membrane separation.

4. The process of claim 2, wherein at least 60% by mass of rhodium in the permeate stream after the membrane separation is separated off by adsorption.

5. The process of claim 1, wherein the single stage membrane has a separation limit in a range from 200 to 2000 g/mol.

6. The process of claim 1, wherein the separating is carried out at a temperature range from 40 to 150° C.

7. The process of claim 1, wherein the separating is carried out at a transmembrane pressure range from 0.5 to 7 MPa.

8. The process of claim 1, wherein the absorbent material is activated carbon.

9. The process of claim 1, wherein the absorbent comprises a chemically modified silica material.

10. The process of claim 8, wherein a liquid flows over the adsorbent as a bed.

11. The process of claim 10, wherein an eluate from the adsorption of the transitional metal is recirculated to the adsorbent.

12. The process of claim 1, wherein the adsorption of the transitional metal is carried out at a temperature range from 30 to 140° C.

13. The process of claim 1, wherein the adsorption of the transitional metal is carried out at a space velocity in a range from 0.01 to 5 l/h.

14. The process of claim 1, wherein the adsorption of the transitional metal is carried out in a fixed bed.

15. The process of claim 2, wherein a product mixture comprising at least one compound selected from the group consisting of a tridecanal and a tridecanol is prepared, and
   wherein removal of rhodium-comprising catalyst complex in the reaction mixture comprises:

a) thermally separating the product mixture from the reaction mixture from a hydroformylation, to obtain a first composition;
b) separating the first composition in an at least single-stage membrane separation which is carried out over at least one membrane so that at least 60% by mass of rhodium present remains in a retentate stream, to obtain a permeate stream;
c) introducing the permeate stream obtained into a subsequent adsorption so that at least 60% by mass of the rhodium present in the permeate stream is retained;
d) recirculating the retentate stream with a concentrated rhodium-comprising catalyst complex from step b) to the hydroformylation.

16. The process of claim 2, wherein at least 60% by mass of rhodium remains in the retentate stream in the separating.

17. The process of claim 2, wherein at least 60% by mass of rhodium in the permeate stream after the separating is separated by adsorption.

18. The process of claim 3, wherein at least 60% by mass of rhodium in the permeate stream after the separating is separated off by adsorption.

19. The process of claim 2, wherein the separating is carried out with a separation limit in a range from 200 to 2000 g/mol.

20. The process of claim 3, wherein the separating is carried out with a separation limit in a range from 200 to 2000 g/mol.

* * * * *